United States Patent
Kincaid et al.

(10) Patent No.: US 10,889,686 B2
(45) Date of Patent: Jan. 12, 2021

(54) BENZOTHIAZOLES AS LATENT CATALYSTS FOR BENZOXAZINE RESINS

(71) Applicant: Huntsman Advanced Materials Americas LLC, The Woodlands, TX (US)

(72) Inventors: Derek Scott Kincaid, Spring, TX (US); Dong Le, Richmond, TX (US); David L. Johnson, The Woodlands, TX (US)

(73) Assignee: HUNTSMAN ADVANCED MATERIALS AMERICAS LLC, The Woodlands, TX (US)

( * ) Notice: Subject to any disclaimer, the term of this patent is extended or adjusted under 35 U.S.C. 154(b) by 0 days.

(21) Appl. No.: 16/300,437

(22) PCT Filed: May 9, 2017

(86) PCT No.: PCT/US2017/031695
§ 371 (c)(1),
(2) Date: Nov. 9, 2018

(87) PCT Pub. No.: WO2017/196805
PCT Pub. Date: Nov. 16, 2017

(65) Prior Publication Data
US 2019/0225752 A1 Jul. 25, 2019

Related U.S. Application Data

(60) Provisional application No. 62/333,937, filed on May 10, 2016.

(51) Int. Cl.
*C08G 73/06* (2006.01)
*C08J 5/24* (2006.01)
(Continued)

(52) U.S. Cl.
CPC .......... *C08G 73/06* (2013.01); *B01J 31/0235* (2013.01); *C07D 265/14* (2013.01);
(Continued)

(58) Field of Classification Search
CPC ........ C08G 14/04; C08G 14/00; C08G 14/12; C08G 73/22; C08L 79/04
See application file for complete search history.

(56) References Cited

U.S. PATENT DOCUMENTS 3,595,900 A  7/1971  Loudas et al.
3,733,349 A  5/1973  Loudas
(Continued)

FOREIGN PATENT DOCUMENTS

EP  2336221 A1  6/2011
WO  2008034753 A1  3/2008
(Continued)

OTHER PUBLICATIONS

Ye et al. (Derwent 2015-42054H), 2015.*
(Continued)

*Primary Examiner* — Shane Fang
(74) *Attorney, Agent, or Firm* — Huntsman Advanced Materials Americas LLC; Lewis D. Craft

(57) ABSTRACT

A curable system containing a benzoxazine and a benzothiazole sulfenamide. The curable system may be catalyzed at temperatures generally used to cure multifunctional epoxy resins yet exhibits improved pot-life and processing times and provides a cured article that exhibits acceptable thermo mechanical properties.

12 Claims, 1 Drawing Sheet

(51) Int. Cl.
  *C07D 265/16* (2006.01)
  *B01J 31/02* (2006.01)
  *C07D 265/14* (2006.01)

(52) U.S. Cl.
  CPC .............. *C07D 265/16* (2013.01); *C08J 5/24* (2013.01); *C08J 2363/00* (2013.01); *C08J 2379/00* (2013.01)

(56) References Cited

U.S. PATENT DOCUMENTS

| | | |
|---|---|---|
| 3,962,184 A | 6/1976 | Notomi et al. |
| 4,022,755 A | 5/1977 | Tanigaichi et al. |
| 4,026,913 A | 5/1977 | Tanigaichi et al. |
| 4,116,946 A | 9/1978 | Jakob et al. |
| 4,195,132 A | 3/1980 | Grigat et al. |
| 4,528,366 A | 7/1985 | Woo et al. |
| 4,709,008 A | 11/1987 | Shimp |
| 4,740,584 A | 4/1988 | Shimp |
| 6,225,440 B1 | 5/2001 | Ishida |
| 7,649,060 B2 | 1/2010 | Li et al. |
| 2005/0196906 A1 | 9/2005 | Shi et al. |
| 2006/0213605 A1 | 9/2006 | Kakubo et al. |
| 2010/0294676 A1 | 11/2010 | Grun et al. |
| 2012/0318571 A1 | 12/2012 | Tietze et al. |
| 2012/0329945 A1 | 12/2012 | Mori et al. |
| 2014/0073736 A1 | 3/2014 | Zahr |
| 2015/0218429 A1 | 8/2015 | Salnikov et al. |
| 2016/0083582 A1 | 3/2016 | Fukuda et al. |

FOREIGN PATENT DOCUMENTS

| | | |
|---|---|---|
| WO | 200915488 A1 | 2/2009 |
| WO | 2011047939 A1 | 4/2011 |
| WO | 2012134731 A1 | 10/2012 |

OTHER PUBLICATIONS

International Search Report and Written Opinion of the International Searching Authority for patent application No. PCT/EP2017/031695, dated Aug. 11, 2017, 7 pages.

\* cited by examiner

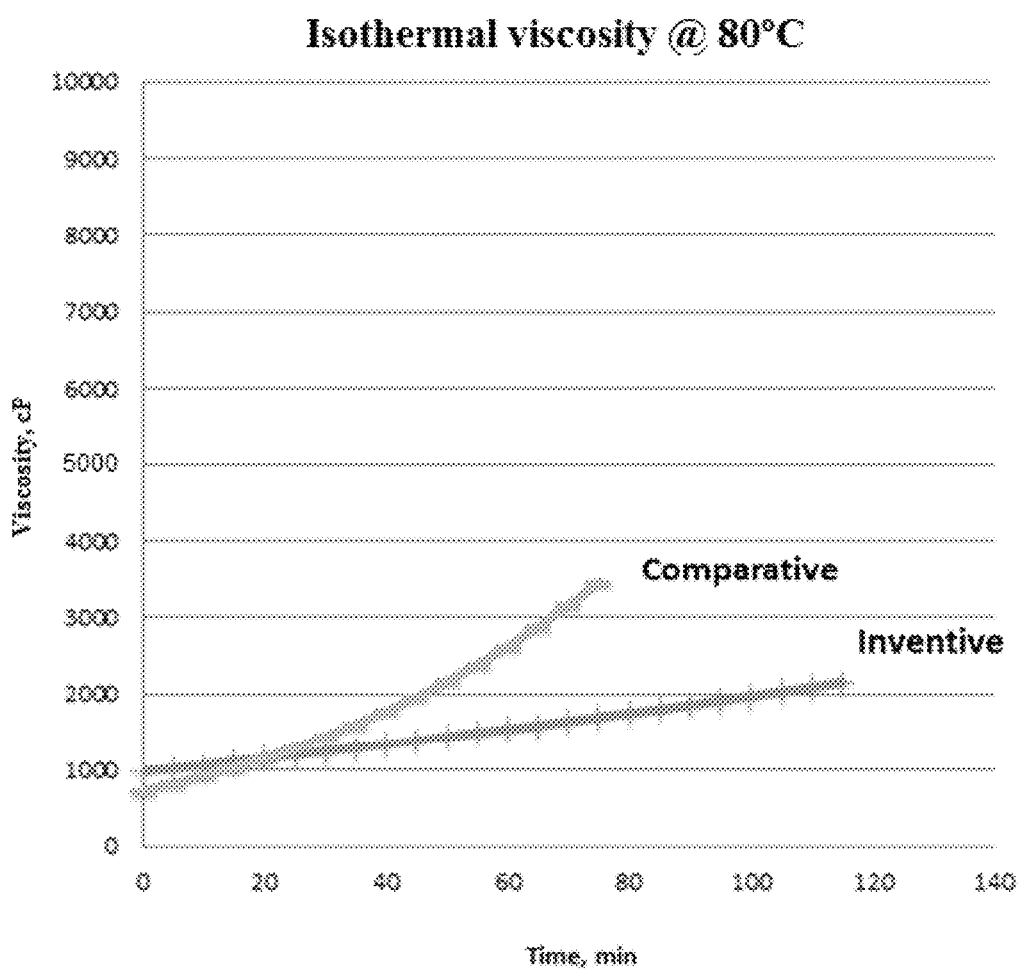

US 10,889,686 B2

BENZOTHIAZOLES AS LATENT CATALYSTS FOR BENZOXAZINE RESINS

CROSS-REFERENCE TO RELATED APPLICATION

This application claims the benefit of U.S. Provisional Patent Application Ser. No. 62/333,937, filed May 10, 2016, the entire disclosures of which are incorporated herein by reference.

STATEMENT REGARDING FEDERALLY SPONSORED RESEARCH OR DEVELOPMENT

Not applicable.

FIELD OF INVENTION

This disclosure relates to a curable system containing a benzoxazine and a benzothiazole sulfenamide catalyst. The curable system is useful in a variety of applications, for example, in an adhesive, sealant, coating, structural composite or encapsulating system for electronic and electrical components.

BACKGROUND

Polymers derived from the ring opening polymerization of benzoxazines compete with phenolic, epoxy and other thermoset or thermoplastic resins in various applications, such as in prepregs, laminates, PWB's, molding compounds, sealants, sinter powders, cast articles, structural composites and electrical components. The benzoxazines, which are synthesized from the reaction of a phenol with an amine and an aldehyde in the presence or absence of a solvent, have been shown to exhibit, upon curing, dimensional stability with good electrical and mechanical resistance, low shrinkage, low water absorption, and medium to high glass transition temperatures.

One drawback to the use of benzoxazines over epoxy resins is that higher cure temperatures are required. Thus, numerous studies have been performed to try to improve the catalysis of the benzoxazine cure reaction so that it is comparable to that for an epoxy resin. For example: U.S. Pat. No. 6,225,440 describes the use of Lewis acids as catalysts for the polymerization of benzoxazine monomers; WO 2008/034753 describes an imidazole/sulfonic acid blend and its use in catalyzing the curing of benzoxazine resins at low temperature; WO 2011/047939 discloses sulfonic acid esters having a cyclic structure which can be used to cure benzoxazine compounds at temperatures between 130° C.-160° C.; WO 2012/134731 teaches the use of a primary amine and superacid to lower the cure temperature of a benzoxazine resin; and, EP2336221 A1 describes the use of lithium salts as catalysts for curing benzoxazine resins.

While state of the art catalysts may be effective in lowering the curing temperature and/or curing time of benzoxazine resin systems, they have a tendency to reduce the pot-life/working time of the systems. In addition, the cured benzoxazine system may exhibit a reduced glass transition temperature as well as properties that do not meet Fire/Smoke/Toxicity ("FST") requirements.

Notwithstanding the state of the technology, it is an object of the present disclosure to provide an improved benzoxazine-based system comprising a catalyst that allows for a controlled and complete polymerization of the benzoxazine resin at low temperatures and/or within shorter curing time without reducing the pot-life of the system or the thermo mechanical properties of the cured product.

SUMMARY

The present disclosure provides a curable system that includes a benzoxazine and a benzothiazole sulfenamide catalyst. In one embodiment, the curable system exhibits a degree of cure of about 80% or higher and provides a cured product exhibiting an acceptable glass transition temperature, FST properties and thermo mechanical properties.

The curable system according to the present disclosure may be used in a variety of applications such as in a coating, adhesive, sealant, or structural composite for use in various industries, such as in the aerospace, automotive or electronic industries.

BRIEF DESCRIPTION OF THE DRAWINGS

FIG. 1 depicts the isothermal viscosity of curable systems over a period of time.

DETAILED DESCRIPTION

If appearing herein, the term "comprising" and derivatives thereof are not intended to exclude the presence of any additional component, step or procedure, whether or not the same is disclosed herein. In order to avoid any doubt, all compositions claimed herein through use of the term "comprising" may include any additional additive, adjuvant, or compound, unless stated to the contrary. In contrast, the term, "consisting essentially of" if appearing herein, excludes from the scope of any succeeding recitation any other component, step or procedure, excepting those that are not essential to operability and the term "consisting of", if used, excludes any component, step or procedure not specifically delineated or listed. The term "or", unless stated otherwise, refers to the listed members individually as well as in any combination.

The articles "a" and "an" are used herein to refer to one or to more than one (i.e., to at least one) of the grammatical object of the article. By way of example, "a benzoxazine" means one benzoxazine or more than one benzoxazine. The phrases "in one embodiment," "according to one embodiment," and the like generally mean the particular feature, structure, or characteristic following the phrase is included in at least one embodiment of the present invention, and may be included in more than one embodiment of the present disclosure. Importantly, such phases do not necessarily refer to the same embodiment. If the specification states a component or feature "may", "can", "could", or "might" be included or have a characteristic, that particular component or feature is not required to be included or have the characteristic.

The term "pot-life" as used herein may be defined as the period of time a curable system is generally fit for its intended purpose under normal environmental conditions without special precautions. For most systems, these normal conditions are processing temperatures up to 120° C. The pot-life of a curable benzoxazine system is usually the period of time until gelation or hardening occurs, thereby making the system difficult or impossible to apply.

The present disclosure generally relates to a curable system containing a benzoxazine and a benzothiazole sulfenamide. Applicants have surprisingly found that the benzothiazole sulfenamide catalyst is effective in not only reducing the energy required to cure the benzoxazine but also increases the pot life and processing time of the system as compared to state of the art catalysts. Moreover, it was unexpectedly found that the benzothiazole sulfenamide catalyst is especially effective in catalyzing benzoxazine systems designed for FST performance to provide a cured product that is capable of passing FST testing while retaining essential thermo mechanical properties.

According to one embodiment, the curable system contains a benzoxazine. The benzoxazine, which imparts mechanical strength, high temperature resistance, low water absorption and thermal curability to the system, may be any curable monomer, oligomer or polymer containing at least one benzoxazine moiety.

Thus, in one embodiment, the benzoxazine may be represented by the general formula

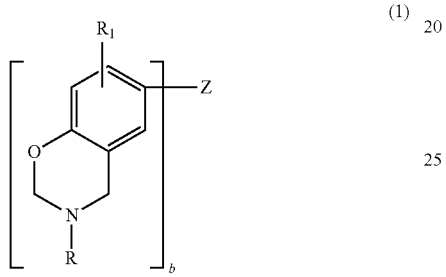

(1)

where b is an integer from 1 to 4; each R is independently hydrogen, a substituted or unsubstituted $C_1$-$C_{20}$ alkyl group, a substituted or unsubstituted $C_2$-$C_{20}$ alkenyl group, a substituted or unsubstituted $C_6$-$C_{20}$ aryl group, a substituted or unsubstituted $C_2$-$C_{20}$ heteroaryl group, a substituted or unsubstituted $C_4$-$C_{20}$ carbocyclic group, a substituted or unsubstituted $C_2$-$C_{20}$ heterocyclic group, or a $C_3$-$C_8$ cycloalkyl group; each $R_1$ is independently hydrogen, a $C_1$-$C_{20}$ alkyl group, a $C_2$-$C_{20}$ alkenyl group, or a $C_6$-$C_{20}$ aryl group; and Z is a direct bond (when b=2), a substituted or unsubstituted $C_1$-$C_{20}$ alkyl group, a substituted or unsubstituted $C_6$-$C_{20}$ aryl group, a substituted or unsubstituted $C_2$-$C_{20}$ heteroaryl group, O, S, S=O, O=S=O or C=O. Substituents include, but are not limited to, hydroxy, a $C_1$-$C_{20}$ alkyl group, a $C_2$-$C_{10}$ alkoxy group, mercapto, a $C_3$-$C_8$ cycloalkyl group, a $C_6$-$C_{14}$ heterocyclic group, a $C_6$-$C_{14}$ aryl group, a $C_6$-$C_{14}$ heteroaryl group, halogen, cyano, nitro, nitrone, amino, amido, acyl, oxyacyl, carboxyl, carbamate, sulfonyl, sulfenamide, and sulfuryl.

In a particular embodiment within formula (1), the benzoxazine may be represented by the following formula:

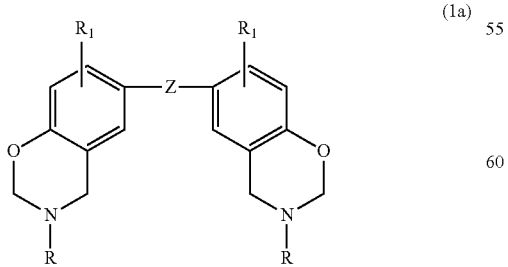

(1a)

where Z is selected from a direct bond, $CH_2$, $C(CH_3)_2$, C=O, O, S, S=O, O=S=O,

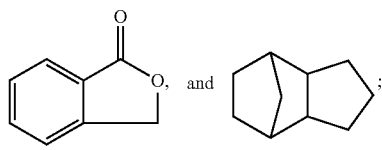 [SMILES: O=C1OCc2ccccc21 ; C1CC2C3CCC(C3)C2C1]

each R is independently hydrogen, a $C_1$-$C_{20}$ alkyl group, an allyl group, or a $C_6$-$C_{14}$ aryl group; and $R_1$ is defined as above.

In another embodiment, the benzoxazine may be embraced by the following general formula

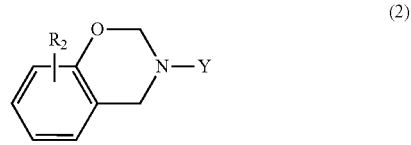

(2)

where Y is a $C_1$-$C_{20}$ alkyl group, a $C_2$-$C_{20}$ alkenyl group, or substituted or unsubstituted phenyl; and each $R_2$ is independently hydrogen, halogen, a $C_1$-$C_{20}$ alkyl group, or a $C_2$-$C_{20}$ alkenyl group. Suitable substituents for phenyl are as set forth above.

In a particular embodiment within formula (2), the benzoxazine may be represented by the following formula

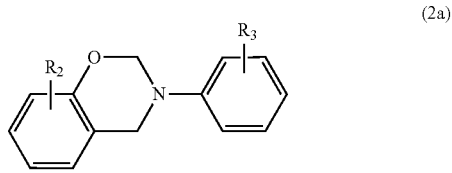

(2a)

where each $R_2$ is independently a $C_1$-$C_{20}$ alkyl or $C_2$-$C_{20}$ alkenyl group, each of which is optionally substituted or interrupted by one or more O, N, S, C=O, COO and NHC=O or a $C_6$-$C_{20}$ aryl group; and each $R_3$ is independently hydrogen, a $C_1$-$C_{20}$ alkyl group or $C_2$-$C_{20}$ alkenyl group, each of which is optionally substituted or interrupted by one or more O, N, S, C=O, COOH and NHC=O or a $C_6$-$C_{20}$ aryl group Alternatively, the benzoxazine may be embraced by the following general formula

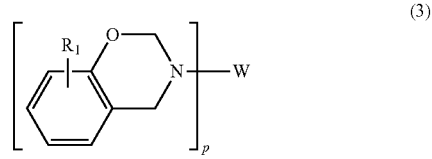

(3)

where p is 2, W is selected from biphenyl, diphenyl methane, diphenyl isopropane, diphenyl sulfide, diphenyl sulfoxide, diphenyl sulfone, and diphenyl ketone, and $R_1$ is defined as above.

In the present disclosure, combinations of multifunctional benzoxazines, combinations of monofunctional benzoxazines, or combinations of one or more multifunctional benzoxazines and one or more monofunctional benzoxazines may be used.

The benzoxazines are commercially available from several sources including Huntsman Advanced Materials Americas LLC under the ARALDITE® brand such as ARALDITE® MT 35600, 35610, 35710 and 35910 resins, Henkel Corporation and Shikoku Chemicals Corporation.

The benzoxazines may also be obtained by reacting a phenol compound, for example, bisphenol A, bisphenol F or phenolphthalein, with an aldehyde, for example, formaldehyde, and a primary amine, under conditions in which water is removed. The molar ratio of phenol compound to aldehyde reactant may be from about 1:3 to 1:10, alternatively from about 1:4 to 1:7. In still another embodiment, the molar ratio of phenol compound to aldehyde reactant may be from about 1:4.5 to 1:5. The molar ratio of phenol compound to primary amine reactant may be from about 1:1 to 1:3, alternatively from about 1:1.4 to 1:2.5. In still another embodiment, the molar ratio of phenol compound to primary amine reactant may be from about 1:2.1 to 1:2.2.

Examples of primary amines include: aromatic mono- or di-amines, aliphatic amines, cycloaliphatic amines and heterocyclic monoamines; for example, aniline, o-, m- and p-phenylene diamine, benzidine, 4,4'-diaminodiphenyl methane, cyclohexylamine, butylamine, methyl amine, hexylamine, allylamine, furfuryl amine, ethylenediamine, and propylenediamine. The amines may, in their respective carbon part, be substituted by $C_1$-$C_8$ alkyl or allyl. In one embodiment, the primary amine is a compound having the general formula $R_aNH_2$, wherein $R_a$ is an allyl, unsubstituted or substituted phenyl, unsubstituted or substituted $C_1$-$C_8$ alkyl or unsubstituted or substituted $C_3$-$C_8$ cycloalkyl. Suitable substituents on the $R_a$ group include, but are not limited to, amino, $C_1$-$C_4$ alkyl and allyl. In some embodiments, one to four substituents may be present on the $R_a$ group. In one particular embodiment, $R_a$ is phenyl.

According to one embodiment, the benzoxazine may be included in the curable system in an amount in the range of between about 10% to about 90% by weight, based on the total weight of the curable system. In another embodiment, the benzoxazine may be included in the curable system in an amount in the range of between about 15% to about 85% by weight, based on the total weight of the curable system. In yet another embodiment, the benzoxazine may be included in the curable system in an amount in the range of between about 20% to about 80% by weight, based on the total weight of the curable system. In still another embodiment, the benzoxazine may be included in the curable system in an amount in the range of between about 25% to about 75% by weight, based on the total weight of the curable system. In embodiments where less shrinkage during curing and higher modulus are desired in the cured article, the benzoxazine may be included in the curable system in an amount in the range of between about 10% to about 25% by weight, based on the total weight of the curable system.

According to another aspect, the curable system contains a benzothiazole sulfenamide. In one embodiment, the benzothiazole sulfenamide is a compound represented by the general formula

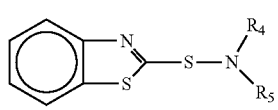

(4)

where $R_4$ and $R_5$ may be the same or different and when taken singly are selected from hydrogen, a branched or unbranched $C_1$-$C_8$ alkyl group, a $C_5$-$C_6$ cycloalkyl group and when taken collectively with the nitrogen atom to which they are attached form a heterocyclic group selected from an azahydrocarbon, an azathiahydrocarbon, an azaoxahydrocarbon and an azaoxathiahydrocarbon. In some embodiments, the benzene ring or heterocyclic ring may have one or more substituents such as halogen, $C_1$-$C_{10}$ alkyl groups or nitro groups.

Examples of the above heterocyclic groups include

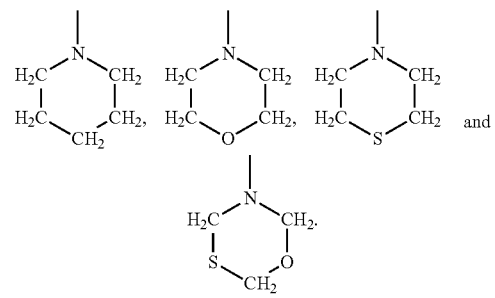

The benzothiazole sulfenamides are commercially available or may be readily prepared by well-known procedures (see, for example, U.S. Pat. Nos. 2,730,526; 2,730,527; 2,758,995; 2,776,297; 2,840,556; 2,981,325; 3,055,909; 3,161,648; 3,658,808). In one embodiment, the benzothiazole sulfenamide may be: N-isopropyl-2-benzothiazole sulfenamide; N,N-diisopropyl-2-benzothiazole sulfenamide; N-t-butyl-2-benzothiazole sulfenamide; N-cyclohexyl-2-benzothiazole sulfenamide; N,N-dicyclohexyl-2-benzothiazole sulfenamide; N-oxydiethyl-2-benzothiazole sulfenamide; 4-morpholinyl-2-benzothiazole disulfide; N-t-octyl-2-benzothiazole sulfenamide; N,N-dicyclopentyl-2-benzothiazole sulfenamide; N,N-diethyl-2-benzothiazole sulfenamide; N-methyl-2-benzothiazole sulfenamide; or, mixtures thereof.

According to one embodiment, the benzothiazole sulfenamide may be included in the curable system in an amount in the range of between about 0.5 parts by weight to about 15 parts by weight, per 100 parts by weight of benzoxazine. In another embodiment, the benzothiazole sulfenamide may be included in the curable system in an amount in the range of between about 1 part by weight to about 10 parts by weight, per 100 parts by weight of benzoxazine. In a further embodiment, the benzothiazole sulfenamide may be included in the curable system in an amount in the range of between about 2 parts by weight to about 8 parts by weight, per 100 parts by weight of benzoxazine. In still a further embodiment, the benzothiazole sulfenamide may be included in the curable system in an amount in the range of between about 3 parts by weight to about 6 parts by weight, per 100 parts by weight of benzoxazine.

According to another aspect, the curable system may optionally contain a diluent. In one embodiment, the diluent is a cycloaliphatic epoxy compound. The cycloaliphatic epoxy compound may be 3',4'-epoxycyclohexylmethyl 3,4-epoxycyclohexanecarboxylate, for example ARALDITE® CY-179 epoxy or CELLOXIDE® 2021 epoxy. In another embodiment, the cycloaliphatic epoxy compound may be a diglycidyl ester of hexahydrophtalic anhydride, for example ARALDITE® CY 184 epoxy. In still another embodiment, the cycloaliphatic epoxy compound may be limonene monoepoxide or limonene diepoxide, for example CELLOXIDE® 3000 epoxy. In a further embodiment, the cycloaliphatic epoxy compound may be cyclohexane oxide, vinyl cyclohexene oxide or vinyl cyclohexene dioxide. According to another embodiment, the cycloaliphatic compound may be bis(3,4-epoxycyclohexylmethyl)adipate, bis (2,3-epoxy cyclopentyl) ether, (3,4-epoxy cyclohexene) methyl alcohol, 2-(3,4-epoxycyclohexyl 5,5-spiro-3,4-epoxy) cyclohexane-metadioxane, 3,4-epoxycyclohexylmethyl-3',4'epoxycyclohexanecarboxylate modified e-caprolactone, (3,4-epoxy cyclohexyl) methyl acrylate, and (3,4-epoxy cyclohexyl) methyl methacrylate. The above cycloaliphatic epoxy compounds may be used alone or as mixtures.

According to an embodiment, the diluent, when present, may be included in the curable system in an amount in the range of between about 0.5 parts by weight to about 45 parts by weight, per 100 parts by weight of benzoxazine. In another embodiment, the diluent may be included in the curable system in an amount in the range of between about 1 part by weight to about 35 parts by weight, per 100 parts by weight of benzoxazine. In a further embodiment, the diluent may be included in the curable system in an amount in the range of between about 2 parts by weight to about 30 parts by weight, per 100 parts by weight of benzoxazine. In yet a further embodiment, the diluent may be included in the curable system in an amount in the range of between about 5 parts by weight to about 25 parts by weight parts, per 100 parts by weight of benzoxazine.

In another aspect, the curable system may optionally include a carrier. According to one embodiment, the carrier may be a polyphenol novolac.

The polyphenol novolacs used in the present disclosure may be prepared according to well-known processes. Such products are described, inter alia, in Houben-Weyl, $4^{th}$ edition, *Methoden der Organischen Chemie*, Vol. E 20, Makromolekulare Stoffe, Part 3, pages 1800-1806, the contents of which are hereby incorporated by reference. For example, the polyphenol novolac may be prepared by reacting formaldehyde or paraformaldehyde with a phenolic compound, such as phenol, methylphenol (cresol), dimethylphenol (xylenol), other alkylphenols, those of bisphenol types, those of biphenyl-phenol or phenyl-phenol types and the like, in the presence or absence of a catalyst such as oxalic acid. The phenolic compound(s), as well as catalytic amounts of oxalic acid, are generally placed in a vessel (with or without solvent or water), and formaldehyde or paraformaldehyde, is added in portions. The volatile components are then removed by distillation under reduced pressure. The polyphenol novolacs may be prepared from one phenolic compound or a mixture of different phenolic compounds.

In one embodiment, the polyphenol novolac is a homopolymer resulting from the condensation of a phenolic compound of formula (5) or (6) with formaldehyde (or paraformaldehyde) or a copolymer of different phenolic compounds of formula (5) and/or (6) with formaldehyde (or paraformaldehyde):

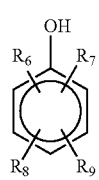
(5)

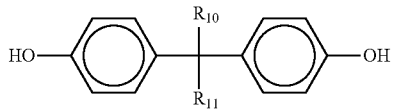
(6)

wherein in formula (5) and (6) $R_6$, $R_7$, $R_8$ and $R_9$, independently of one another, are hydrogen or a branched or unbranched $C_1$-$C_{15}$ alkyl group, and $R_{10}$ and $R_{11}$, independently of each other, are hydrogen, $CH_3$ or $CF_3$.

In one embodiment, the polyphenol novolacs derived from compounds of formula (5) are those wherein in formula (5) $R_6$, $R_7$, $R_8$ and $R_9$ are either H (phenol), or wherein, while the remaining radicals $R_6$, $R_7$, $R_8$ and $R_9$ are H, one or two of the radicals $R_6$, $R_7$, $R_8$ and $R_9$ are the radical —$CH_3$, or one of the radicals $R_6$, $R_7$, $R_8$ and $R_9$ is a tert-butyl radical, or one of the radicals $R_6$, $R_7$, $R_8$ and $R_9$ is a branched or unbranched $C_8$-$C_{15}$ alkyl group.

In another embodiment, the polyphenol novolacs derived from compounds of formula (6) are those, wherein in formula (6), $R_{10}$ and $R_{11}$ are both either hydrogen or $CH_3$.

According to this disclosure for a polyphenol novolac being a copolymer of different phenolic compounds of formula (5) and/or (6) with formaldehyde (or paraformaldehyde), it is understood that the polyphenol novolac results from using a mixture of at least two different phenolic compounds when synthesizing the polyphenol novolac.

According to one embodiment, when present, the carrier may be included in the curable system in an amount in the range of between about 0.5 parts by weight to about 30 parts by weight, per 100 parts by weight of benzoxazine. In another embodiment, the carrier may be included in the curable system in an amount in the range of between about 1 part by weight to about 25 parts by weight, per 100 parts by weight of benzoxazine. In a further embodiment, the carrier may be included in the curable system in an amount in the range of between about 2 parts by weight to about 20 parts by weight, per 100 parts by weight of benzoxazine. In still a further embodiment, the carrier may be included in the curable system in an amount in the range of between about 5 parts by weight to about 15 parts by weight, per 100 parts by weight of benzoxazine.

In another aspect, the curable system may optionally include a toughener. Examples of tougheners which may be used include copolymers based on butadiene/acrylonitrile, butadiene/(meth)acrylic acid esters, butadiene/acrylonitrile/styrene graft copolymers ("AB S"), butadiene/methyl methacrylate/styrene graft copolymers ("MBS"), poly(propylene) oxides, amine-terminated butadiene/acrylonitrile copolymers ("ATBN") and hydroxyl-terminated polyether sulfones, such as PES 5003P toughener, available commercially from Sumitomo Chemical Company or RADEL® brand tougheners from Solvay Advanced Polymers, LLC, core shell rubber and polymers, such as PS 1700 tougheners, rubber particles having a core-shell structure in an epoxy resin matrix such as MX-120 resin from Kaneka Corporation, GENIOPEARL® M23A resin from Wacker Chemie GmbH, a rubber-modified epoxy resin, for instance an epoxy-terminated adduct of an epoxy resin and a diene rubber or a conjugated diene/nitrile rubber.

According to one embodiment, when present, the toughener may be included in the curable system in an amount in the range of between about 0.5 parts by weight to about 35 parts by weight, per 100 parts by weight of benzoxazine. In another embodiment, the toughener may be included in the curable system in an amount in the range of between about 1 part by weight to about 30 parts by weight, per 100 parts by weight of benzoxazine. In a further embodiment, the toughener may be included in the curable system in an amount in the range of between about 2 parts by weight to about 25 parts by weight, per 100 parts by weight of benzoxazine. In still a further embodiment, the toughener may be included in the curable system in an amount in the range of between about 5 parts by weight to about 20 parts by weight, per 100 parts by weight of benzoxazine.

In another aspect, the curable system may optionally include a modifier. In one embodiment, the modifier is a cyanate ester or bismaleimide. The cyanate ester may be monomeric, oligomeric, or polymeric, with at least one cyanate ester compound in the composition having at least two cyanate ester functional groups (—OCN) per molecule. Such cyanate esters may include polyaromatic cyanate esters, such as cyanate esters of bisphenols or cyanate esters of polymeric dicyclopentadiene structures. Useful cyanate esters include, but are not limited to the following: 1,3- and 1,4-dicyanatobenzene; 2-tert-butyl-1,4-dicyanatobenzene; 2,4-dimethyl-1,3-dicyanatobenzene; 2,5-di-tert-butyl-1,4-dicyanatobenzene; tetramethyl-1,4-dicyanatobenzene; 4-chloro-1,3-dicyanatobenzene; 1,3,5-tricyanatobenzene; 2,2'- and 4,4'-dicyanatobiphenyl; 3,3'5,5'-tetramethyl-4,4'-dicyanatobiphenyl; 1,3-, 1,4-, 1,5-, 1,6-, 1,8-, 2,6-, and 2,7-dicyanatonaphthalene; 1,3,6-tricyanatonaphthalene; bis(4-cyanatophenyl)methane; bis(3-chloro-4-cyanatophenyl)methane; bis(3,5-dimethyl-4-cyanatophenyl)methane; 1,1-bis(4-cyanatophenyl)ethane; 2,2-bis(4-cyanatophenyl)propane; 2,2-bis(3,3-dibromo-4-cyanatophenyl)propane; 2,2-bis(4-cyanatophenyl)-1,1,1,3,3,3-hexafluoropropane; bis(4-cyanatophenyl)ester; bis(4-cyanatophenoxy)benzene; bis(4-cyanatophenyl)ketone; bis(4-cyanatophenyl)thioether; bis(4-cyanatophenyl)sulfone; tris(4-cyanatophenyl)phosphate, and tris(4-cyanatophenyl)phosphate. Also useful are cyanic acid esters derived from phenolic resins, for example, as disclosed in U.S. Pat. No. 3,962,184, cyanated novolac resins derived from novolac, for example, as disclosed in U.S. Pat. No. 4,022,755, cyanated bis-phenol-type polycarbonate oligomers derived from bisphenol-type polycarbonate oligomers, as disclosed in U.S. Pat. No. 4,026,913, cyano-terminated polyarylene ethers as disclosed in U.S. Pat. No. 3,595,900, and dicyanate esters free of ortho hydrogen atoms as disclosed in U.S. Pat. No. 4,740,584, mixtures of di- and tricyanates as disclosed in U.S. Pat. No. 4,709,008, polyaromatic cyanates containing polycyclic aliphatic groups as disclosed in U.S. Pat. No. 4,528,366, fluorocarbon cyanates as disclosed in U.S. Pat. No. 3,733,349, and cyanates disclosed in U.S. Pat. Nos. 4,195,132, and 4,116,946, all of the foregoing patents being incorporated by reference. Polycyanate compounds obtained by reacting a phenol-formaldehyde precondensate with a halogenated cyanide are also useful.

The bismaleimide may include 4,4'-bismaleimido-diphenylmethane, 1,4-bismaleimido-2-methylbenzene and mixtures thereof; modified and partially advanced modified bismaleimide resins containing Diels-Alder comonomers; and a partially advanced bismaleimide based on 4,4'-bismaleimido-diphenylmethane and allylphenyl compounds or aromatic amines. Examples of suitable Diels-Alder comonomers include styrene and styrene derivatives, bis(propenylphenoxy) compounds, 4,4'-bis(propenylphenoxy) sulfones, 4,4'-bis(propenylphenoxy)benzophenones and 4,4'4-(1-methyl ethylidene) bis(2-(2-propenyl)phenol). Examples of commercially available modified bismaleimides based on 4,4'-bismaleimido-diphenylmethane and an allylphenyl compound, such as diallylbisphenol-A, are MATRIMID® 5292A and MATRIMID® 5292B resins. Other bismaleimides include Michael addition copolymers of bismaleimide and aromatic diamines, such as 4,4'-bismaleimido-diphenylmethane/4,4'-diaminodiphenylmethane.

Still other bismaleimides are higher molecular weight bismaleimides produced by advancement reactions of the aforementioned bismaleimide resins. Exemplary bismaleimide resins are those based on 4,4'-bismaleimido-diphenylmethane. Mixtures of cyanate esters and bismaleimides may also be used.

According to one embodiment, the modifier, when present, may be included in the curable system in an amount in the range of between about 0.1 parts by weight to about 40 parts by weight, per 100 parts by weight of benzoxazine. In further embodiments, the modifier may be included in the curable system in an amount in the range of between about 2 parts by weight to about 20 parts by weight, per 100 parts by weight of benzoxazine. In still another embodiment, the modifier may be included in the curable system in an amount in the range of between about 3 parts to about 10 parts by weight, per 100 parts by weight of benzoxazine.

In a further aspect, the curable system may optionally include one or more additives. Examples of such additives, include, but are not limited to, an additional catalyst, reinforcing agent, filler and mixtures thereof.

Examples of additional catalysts which may be used include amines, polyaminoamides, imidazoles, phosphines, and metal complexes of organic sulfur containing acid as described in WO 200915488, which is incorporated herein by reference.

Examples of filler and reinforcing agents which may be used include silica, silica nanoparticles, coal tar, bitumen, textile fibres, glass fibres, asbestos fibres, boron fibres, carbon fibres, mineral silicates, mica, powdered quartz, hydrated aluminum oxide, bentonite, wollastonite, kaolin, aerogel or metal powders, for example aluminum powder or iron powder, and also pigments and dyes, such as carbon black, oxide colors and titanium dioxide, light weight microballoons, such as cenospheres, glass microspheres, carbon and polymer microballoons, fire-retarding agents, thixotropic agents, flow control agents, such as silicones, waxes and stearates, which can, in part, also be used as mold release agents, adhesion promoters, antioxidants and light stabilizers, the particle size and distribution of many of which may be controlled to vary the physical properties and performance of the inventive compositions.

According to one embodiment, the additive(s), when present, may be included in the curable system in an amount in the range of between about 0.1 parts by weight to about 30 parts by weight, per 100 parts by weight of benzoxazine. In further embodiments, the additive(s) may be included in the curable system in an amount in the range of between about 2 parts by weight to about 20 parts by weight, per 100 parts by weight of benzoxazine. In still another embodiment, the additive(s) may be included in the curable system in an amount in the range of between about 5 parts by weight to about 15 parts by weight, per 100 parts by weight of benzoxazine.

In another embodiment, there is provided a curable system comprising
 (i) a benzoxazine;
 (ii) 0.5-15 parts by weight, per 100 parts by weight of benzoxazine, of a benzothiazole sulfenamide;
 (iii) optionally 0.5-45 parts by weight, per 100 parts by weight of benzoxazine, of a cycloaliphatic epoxy compound;

(iv) optionally 0.5-30 parts by weight, per 100 parts by weight of benzoxazine, of a polyphenol novolac;

(v) optionally 0.5-35 parts by weight, per 100 parts by weight of benzoxazine, of a toughener; and (vi) optionally 0.1-40 parts by weight, per 100 parts by weight of benzoxazine, of a cyanate ester or bismaleimide The curable system according to the present disclosure may be prepared by methods known, for example, by combining the benzoxazine, benzothiazole sulfenamide catalyst and optional component(s) discussed above with the aid of known mixing units such as kneaders, stirrers, rollers, in mills or in dry mixers. Thus, in one embodiment, the curable system is provided as a one-component system comprising the benzoxazine, benzothiazole and optional diluent, carrier, toughener, modifier and/or additives. Time and temperature of the method of preparation is not critical, but generally the benzoxazine, benzothiazole sulfenamide and optional component(s) can be mixed at a temperature ranging from about 10° C. to about 120° C. and in some embodiments from about 20° C. to about 60° C. In other embodiments, the benzoxazine, benzothiazole sulfenamide and optional component(s) can be mixed at a temperature from about 90° C. to about 110° C. The mixture is mixed for a sufficient time period until complete homogeneity is achieved.

In another embodiment, the curable system is provided as a two-component system. The two-component system includes a first component Part A housed in a first container including the benzoxazine. The second component Part B, housed in a second container, includes the benzothiazole sulfenamide catalyst. Part A may also include a diluent, carrier, toughener, modifier and additives. Additionally, Part B may also include a diluent, carrier, toughener, modifier and additives. Parts A and B of this curable system are stable under standard storage conditions and Part A may be mixed with Part B before application and curing.

It has been surprisingly found that the benzoxazine and benzothiazole sulfenamide of the present disclosure, when combined, form a curable system that exhibits a long pot-life (in some embodiments up to about 8 hours), a long open-time and a low processing viscosity at temperatures of 125° C. or less and can be cured at relatively low temperatures, preferably at temperatures in the range of about 120° C. to about 160° C. in short time periods, preferably within a time period of about 5 min to 5 hours, and upon curing, produces a cured article that exhibits an excellent balance of thermal, mechanical and physical properties, such as, high glass transition temperature ($T_g$), low coefficient of thermal expansion, low polymerization temperature, low viscosity, high toughness, high mechanical strength, low water absorption, and flame retardancy. Thus, in another embodiment, there is provided a cured article produced by curing the curable system.

In another aspect, the present disclosure provides a process for preparing a resin coated substrate. The process steps include contacting a substrate with the curable system of the present disclosure. Curable systems of the present disclosure may be contacted with the substrate by any method known to those skilled in the art. Examples of such contacting methods include, but are not limited to, dipping, spray coating, die coating, roll coating, resin infusion processes, and contacting the article with a bath containing the curable system. The substrate may be, for example, plastic, glass, alloy, metal, ceramic, wood, cement, concrete, rubber, or reinforcement fiber material.

According to another embodiment, the curable system, once mixed, may be contacted with any suitable substrate and cured according to typical processes practiced by the industry to form a cured product. The expression "cured" as used herein, denotes the conversion of the above curable system into an insoluble and infusible crosslinked product, with simultaneous shaping to give a shaped article such as a molding, pressing or laminate or to give a two-dimensional structure such as a coating, enamel, or adhesive bond. Typical curing processes include ambient temperature cure to elevated temperature cure using thermal, radiation or a combination of energy sources. The curable system may be cured in one step or multiple steps such as A, B staged cures often practiced in the electrical laminates and composites industries. Or, the curable system may be post-cured using a different temperature or energy source after the initial cure cycle.

Accordingly, the present disclosure also provides a cured product obtained by contacting any suitable substrate with the curable system and curing the curable system using thermal, radiation or a combination of energy sources. In one embodiment, the resin coated substrate may be thermally cured by applying heat to the curable system at a temperature of from about 120° C. to about 170° C., preferably from about 130° C. to about 160° C., for a period of time from about 1 minute to about 300 minutes, preferably from about 45 minutes to about 150 minutes. Optionally, molded forms of the cured product may be further post-cured at a temperature of from about 120° C. to about 250° C. for a period of time period from about 30 minutes to about 12 hours under vacuum. In one particular embodiment, the curable system may be cured by heating the curable system at a temperature of between about 120° C.-125° C. for about 0.5-1 hour, followed by heating and curing at a temperature of between about 135° C.-145° C. for about 1.5-2 hours which is then followed by heating and curing the curable system at a temperature of between about 145° C.-155° C. for about 0.5-1.5 hours.

In addition, the curable system of the present disclosure may be used in methods for bonding one or more substrates together by contacting one or more surfaces of like or dissimilar substrates to be bonded with the curable system under conditions sufficient to cure the curable system. Such conditions are those generally used in currently known processes practiced by one skilled in the art and may include application of pressure and/or heat.

As noted above, the curable system is suitable for use as a coating, adhesive, sealant, and matrice for the preparation of reinforced composite material, such as prepregs and towpregs, and can also be used in injection molding or extrusion processes.

Thus, in another embodiment, the present disclosure provides an adhesive, sealant, coating or encapsulating system for electronic or electrical components comprising the curable system of the present disclosure. Suitable substrates on which the coating, sealant, adhesive or encapsulating system comprising the curable system may be applied include metal, such as steel, aluminum, titanium, magnesium, brass, stainless steel, galvanized steel; silicates such as glass and quartz; metal oxides; concrete; wood; electronic chip material, such as semiconductor chip material; or polymers, such as polyimide film and polycarbonate. The adhesive, sealant or coating comprising the curable system may be used in a variety of applications, such as in industrial or electronic applications.

In another embodiment, the present disclosure provides a cured product comprising bundles or layers of fibers infused with the curable system.

In yet another embodiment, the present disclosure provides a method for producing a prepreg or towpreg including the steps of (a) providing a bundle or layer of fibers; (b) providing a curable system of the present disclosure; (c) joining the bundle or layer of fibers and curable system to form a prepreg or towpreg assembly; (d) optionally removing excess curable system from the prepreg or towpreg assembly, and (e) exposing the prepreg or towpreg assembly to elevated temperature and/or pressure conditions sufficient to infuse the bundle or layer of fibers with the curable system and form a prepreg or towpreg.

In some embodiments, the bundle or layer of fibers may be constructed from unidirectional fibers, woven fibers, chopped fibers, non-woven fibers or long, discontinuous fibers. The fibers may be selected from glass, such as S glass, S2 glass, E glass, R glass, A glass, AR glass, C glass, D glass, ECR glass, glass filament, staple glass, T glass and zirconium glass, carbon, polyacrylonitrile, acrylic, aramid, boron, polyalkylene, quartz, polybenzimidazole, polyetherketone, polyphenylene sulfide, poly p-phenylene benzobisoxazole, silicon carbide, phenolformaldehyde, phthalate and naphthenoate.

The curable system and prepregs or towpregs prepared therefrom are particularly useful in the manufacture and assembly of composite parts for aerospace and automotive applications, bonding of composite and metal parts, core and core-fill for sandwich structures and composite surfacing.

EXAMPLES

The following curable systems were produced and cured at the conditions in Table 1 below:

TABLE 1

|  | Curable System Control | Curable System Comparative | Curable System Inventive |
|---|---|---|---|
| Benzoxazine[1] | 100 | 100 | 100 |
| Phenol-based Accelerator |  | 2 |  |
| Polyphenol Novolac |  | 10 | 10 |
| Benzene Sulfenamide (N-oxidiethylene-2-benzene-sulfenamide) |  |  | 4 |
| Viscosity (80° C.) (cP) |  | 723.7 | 982.5 |
| Cure Schedule | 1 hr 150° C. 1.5 hr 177° C. | 0.5 hr 120° C. 2 hr 140° C. 1 hr 150° C. | 0.5 hr 120° C. 2 hr 140° C. 1 hr 150° C. |
| % Cure | NA | 90.80 | 83.00 |
| DSC Onset (° C.) | 212.04 | 150 | 159.63 |
| DSC Peak(° C.) | 226.80 | 183 | 194 |
| Enthalpy (J/g) | 356.5 | 413 | 400 |
| DSC Tg (° C.) | 142 | 128 | 117 |

[1]Bisphenol F-based benzoxazine designed for Fire/Smoke/Toxicity performance.

The Fire/Smoke/Toxicity properties of the curable systems above were then tested and the results are provided in Table 2 below:

TABLE 2

|  | FST Pass Criteria | Curable System Comparative | Curable System Inventive |
|---|---|---|---|
| DMA Tg (° C.) | NA | 125 | 118 |
| Extinction times (min) | <15 | 0 | 0 |
| Burn length (inches) | <6 | 4.1 | 4.9 |
| Drip Ext. time | <3 | 0 | 0 |
| Specific Optical Density (DS) | <20 | 11.1 | 10.8 |
| Total heat release (Kw*min/m²) | <65 | 15.8 | 24.3 |
| Overall | Pass | Pass | Pass |

Finally, FIG. 1 shows the increase in pot life (slower increase in viscosity) of the formulation catalyzed with inventive curable system described above as compared to the comparative curable system.

Although making and using various embodiments of the present disclosure have been described in detail above, it should be appreciated that the present disclosure provides many applicable inventive concepts that can be embodied in a wide variety of specific contexts. The specific embodiments discussed herein are merely illustrative of specific ways to make and use the invention, and do not delimit the scope of the invention.

The invention claimed is:

1. A curable system comprising 20-88 parts by weight, per 100 parts by weight of the curable system, of a benzoxazine and 3.5-15 parts by weight, per 100 parts by weight of the benzoxazine, of a benzothiazole sulfenamide catalyst.

2. The curable system of claim 1, wherein the benzoxazine is a compound represented by the general formula

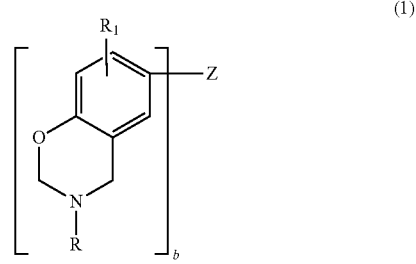

(1)

where b is an integer from 1 to 4; each R is independently hydrogen, a substituted or unsubstituted $C_1$-$C_{20}$ alkyl group, a substituted or unsubstituted $C_2$-$C_{20}$ alkenyl group, a substituted or unsubstituted $C_6$-$C_{20}$ aryl group, a substituted or unsubstituted $C_2$-$C_{20}$ heteroaryl group, a substituted or unsubstituted $C_4$-$C_{20}$ carbocyclic group, a substituted or unsubstituted $C_2$-$C_{20}$ heterocyclic group, or a $C_3$-$C_8$ cycloalkyl group; each $R_1$ is independently hydrogen, a $C_1$-$C_{20}$ alkyl group, a $C_2$-$C_{20}$ alkenyl group, or a $C_6$-$C_{20}$ aryl group; and Z is a direct bond (when b=2), a substituted or unsubstituted $C_1$-$C_{20}$ alkyl group, a substituted or unsubstituted $C_6$-$C_{20}$ aryl group, a substituted or unsubstituted $C_2$-$C_{20}$ heteroaryl group, O, S, S=O, O=S=O or C=O.

3. The curable system of claim 2, wherein the benzoxazine is a compound represented by the formula:

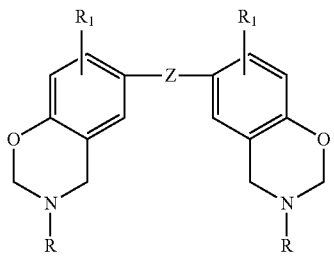

(1a)

where Z is selected from a direct bond, $CH_2$, $C(CH_3)_2$, C=O, O, S, S=O, O=S=O,

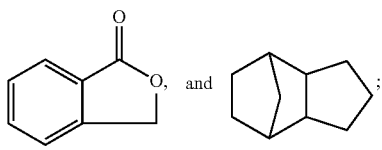 [SMILES: O=C1OCc2ccccc21 ; C1CC2C3CCC(C3)C2C1]

each R is independently hydrogen, a $C_1$-$C_{20}$ alkyl group, an allyl group, or a $C_6$-$C_{14}$ aryl group; and $R_1$ is defined as in claim 2.

4. The curable system of claim 1, wherein the benzothiazole sulfonamide catalyst is a compound represented by the formula

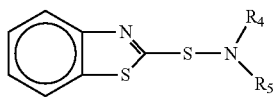

(4)

where $R_4$ and $R_5$ may be the same or different and when taken singly are selected from hydrogen, a branched or unbranched $C_1$-$C_8$ alkyl group and a $C_5$-$C_6$ cycloalkyl group, and when taken collectively with the nitrogen atom to which they are attached form a heterocyclic group selected from an azahydrocarbon, an azathiahydrocarbon, an azaoxahydrocarbon and an azaoxathiahydrocarbon.

5. The curable system of claim 4, wherein the benzothiazole sulfonamide catalyst is N-isopropyl-2-benzothiazole sulfenamide; N,N-diisopropyl-2-benzothiazole sulfenamide; N-t-butyl-2-benzothiazole sulfenamide; N-cyclohexyl-2-benzothiazole sulfenamide; N,N-dicyclohexyl-2-benzothiazole sulfenamide; N-oxydiethyl-2-benzothiazole sulfenamide; 4-morpholinyl-2-benzothiazole disulfide; N-t-octyl-2-benzothiazole sulfenamide; N,N-dicyclopentyl-2-benzothiazole sulfenamide; N,N-diethyl-2-benzothiazole sulfenamide; N-methyl-2-benzothiazole sulfenamide; or mixtures thereof.

6. The curable system of claim 1, further comprising a diluent.

7. The curable system of claim 6, wherein the diluent is a cycloaliphatic epoxy compound.

8. The curable system of claim 1, further comprising a carrier.

9. The curable system of claim 8, wherein the carrier is a polyphenol novolac.

10. The curable system of claim 1, further comprising a toughener.

11. A cured article comprising bundles or layers of fibers infused with the curable system of claim 1.

12. A method for producing a prepreg or towpreg comprising the steps of (a) providing a bundle or layer of fibers; (b) providing the curable system of claim 1; (c) joining the bundle or layer of fibers and curable system to form a prepreg or towpreg assembly; (d) optionally removing excess curable system from the prepreg or towpreg assembly, and (e) exposing the prepreg or towpreg assembly to elevated temperature and/or pressure conditions sufficient to infuse the bundle or layer of fibers with the curable system and form a prepreg or towpreg.

\* \* \* \* \*